United States Patent
Pfister et al.

(10) Patent No.: US 7,680,528 B2
(45) Date of Patent: Mar. 16, 2010

(54) METHOD FOR THE GRAPHICAL REPRESENTATION OF A MEDICAL INSTRUMENT INSERTED AT LEAST PARTIALLY INTO AN OBJECT UNDER EXAMINATION

(75) Inventors: Marcus Pfister, Bubenreuth (DE); Bernhard Sandkamp, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 278 days.

(21) Appl. No.: 11/522,261

(22) Filed: Sep. 15, 2006

(65) Prior Publication Data
US 2007/0083102 A1 Apr. 12, 2007

(30) Foreign Application Priority Data
Sep. 16, 2005 (DE) .................... 10 2005 044 405

(51) Int. Cl.
*A61B 5/05* (2006.01)
(52) U.S. Cl. .................... 600/429; 600/407
(58) Field of Classification Search .................... 600/429
See application file for complete search history.

(56) References Cited

U.S. PATENT DOCUMENTS

| | | | | |
|---|---|---|---|---|
| 4,637,929 | A * | 1/1987 | Quay | 424/9.365 |
| 4,638,798 | A * | 1/1987 | Shelden et al. | 606/130 |
| 4,827,413 | A | 5/1989 | Baldwin et al. | |
| 5,274,551 | A | 12/1993 | Corby, Jr. | |
| 5,937,144 | A * | 8/1999 | Wilkins et al. | 358/1.2 |
| 6,219,522 | B1 * | 4/2001 | Ishizuka et al. | 399/333 |
| 6,259,802 | B1 * | 7/2001 | Jolly et al. | 382/103 |
| 6,542,770 | B2 | 4/2003 | Zylka et al. | |
| 6,640,127 | B1 * | 10/2003 | Kosaka et al. | 600/426 |
| 7,148,907 | B2 * | 12/2006 | Smith et al. | 345/629 |
| 2003/0216634 | A1 * | 11/2003 | van Muiswinkel et al. | 600/410 |
| 2004/0077952 | A1 * | 4/2004 | Rafter et al. | 600/481 |
| 2004/0171924 | A1 * | 9/2004 | Mire et al. | 600/407 |
| 2005/0089143 | A1 | 4/2005 | Nakano et al. | |
| 2005/0165292 | A1 | 7/2005 | Simon et al. | |

FOREIGN PATENT DOCUMENTS

| | | |
|---|---|---|
| DE | 38 32 222 C2 | 3/1990 |
| DE | 100 04 764 A1 | 8/2001 |
| EP | 0 633 548 B1 | 1/1995 |
| WO | WO 2004/044847 A1 | 5/2004 |

OTHER PUBLICATIONS

Sven Behnke, Marcus Pfister and Raul Rojas, "Recognition of Handwritten Digits using Structural Information", Proceedings of International Conference on Neural Networks, ICNN '97, vol. 3, 1997, pp. 1391-1396.

* cited by examiner

*Primary Examiner*—Long V Le
*Assistant Examiner*—Hien Nguyen

(57) ABSTRACT

The invention provides a method for the graphical representation of a medical instrument inserted at least partially into an object under examination, with an image representing the medical instrument being generated, in that the instrument image is vectorized, with the medical instrument being represented as a polyline.

14 Claims, 3 Drawing Sheets

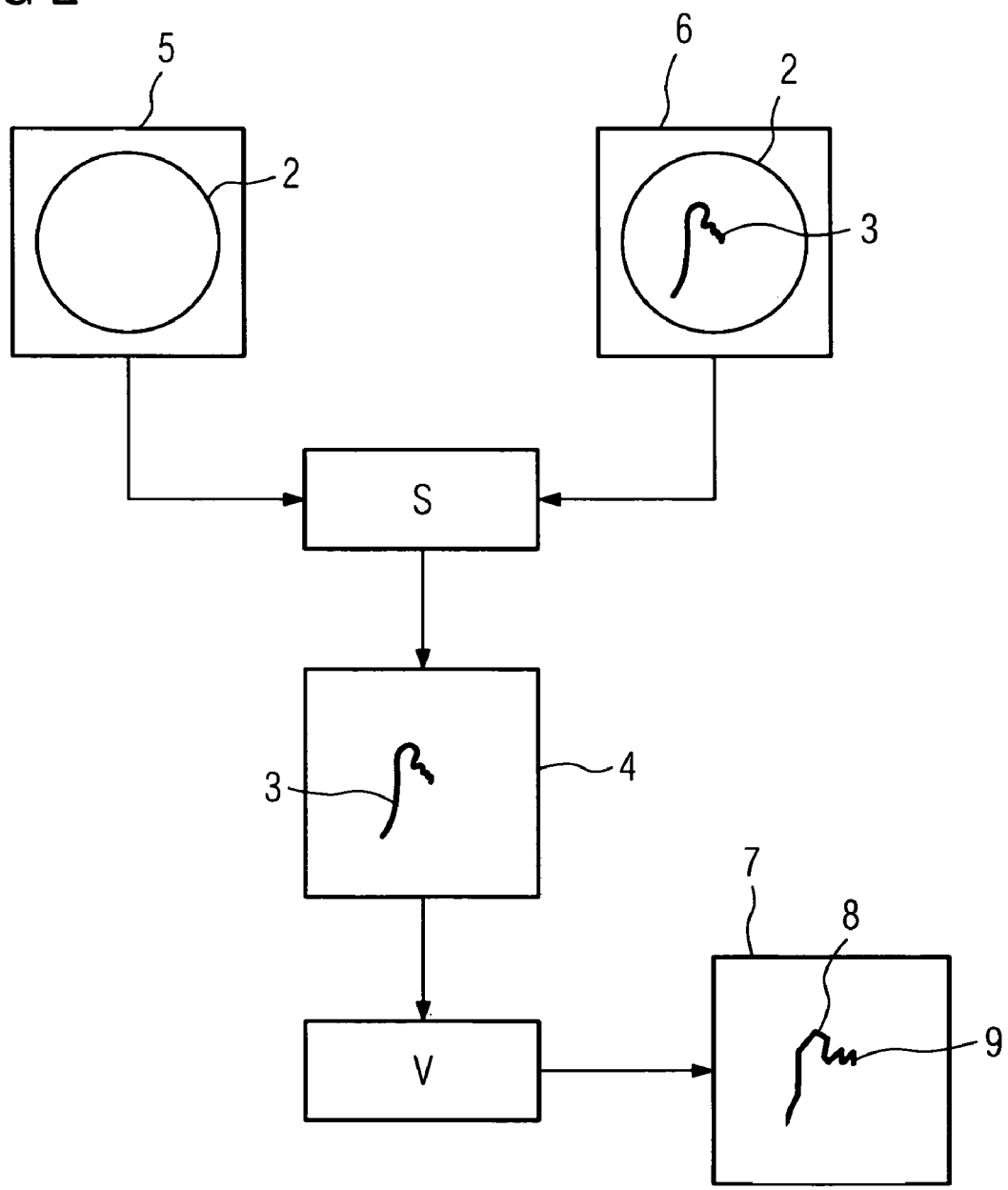

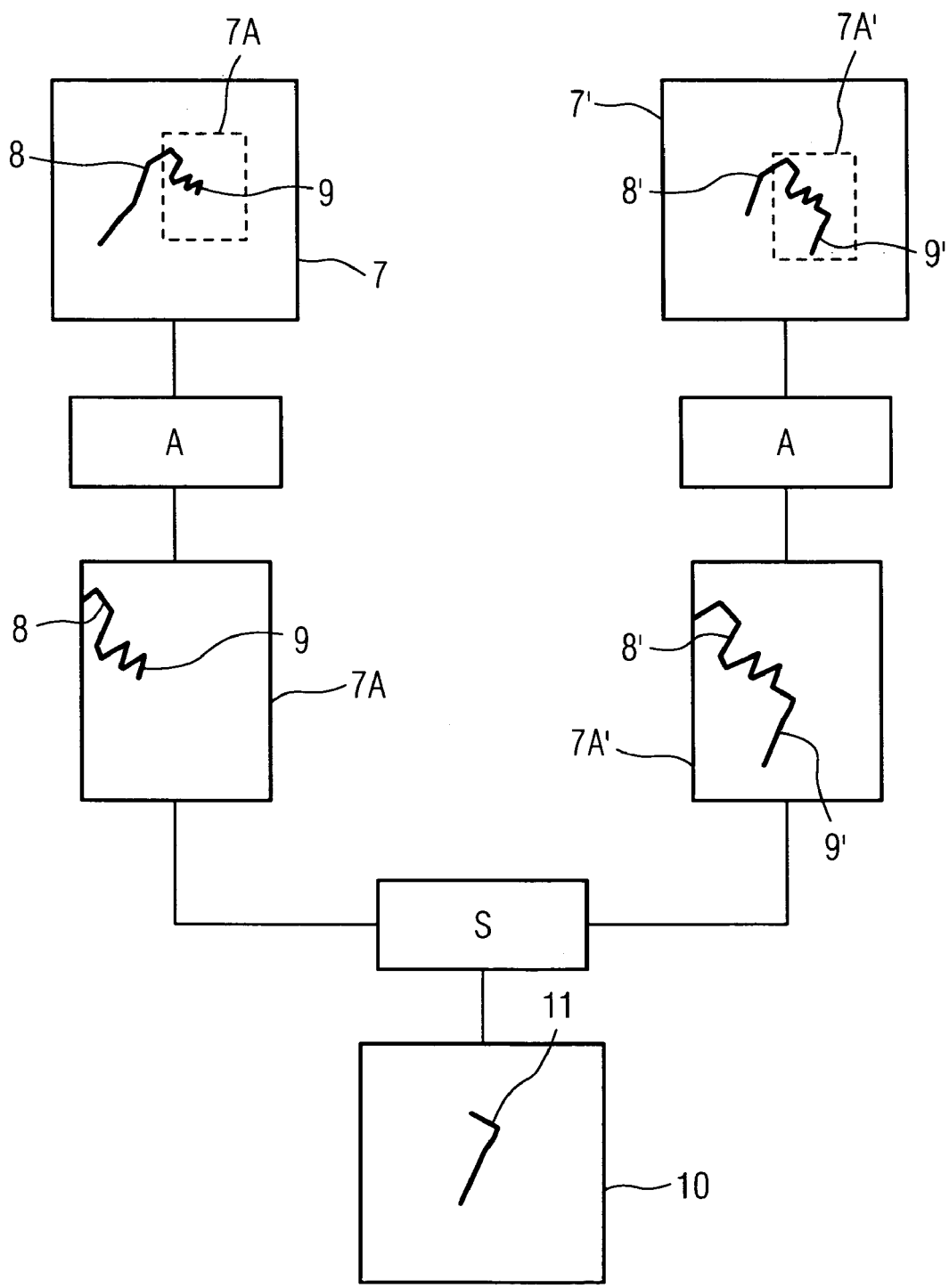

METHOD FOR THE GRAPHICAL REPRESENTATION OF A MEDICAL INSTRUMENT INSERTED AT LEAST PARTIALLY INTO AN OBJECT UNDER EXAMINATION

CROSS REFERENCE TO RELATED APPLICATIONS

This application claims priority of German application No. 10 2005 044 405.9 filed Sep. 16, 2005, which is incorporated by reference herein in its entirety.

FIELD OF THE INVENTION

The invention relates to a method for a graphical representation of a medical instrument inserted at least partially into an object under examination.

BACKGROUND OF THE INVENTION

When a medical intervention is being carried out on an object under examination, perhaps a human or animal body, the status of the object under examination is generally controlled in a manner that is appropriate for the intervention risk. Body functions of the object under examination are recorded for this purpose. In the case of an intervention with a medical device inserted at least partially into the object under examination, the position and/or optionally the location of the medical instrument within the object under examination is of interest as well as patient status.

Examples of medical instruments are catheters, guide wires, stents, sheaths, biopsy needles or other means that are inserted at least partially into the object under examination during medical interventions.

In order to be able to determine the site and/or spatial orientation of the medical instrument, a method is required, which allows the locating—in other words determination of the position and/or location—of the medical instrument. Medical personnel also have to determine any changes in the position and/or location of the medical instrument on a continuous basis, in order to control the insertion into or further progress of the medical instrument in the object under examination. Such a method can increase the accuracy of the intervention, reduce damage to the object under examination and improve patient safety.

A method for determining the position of a medical instrument is known from the published patent application DE 100 04 764 A1. The first method step comprises the pre-operative acquisition of computed tomograms, which make it possible to generate a three-dimensional image data record before the actual medical intervention on the object under examination. This is followed by an intra-operative method step, wherein two-dimensional images are acquired using an x-ray device during the intervention on the object under examination and used to determine the position of the medical instrument.

A position measuring device is also provided for the extracorporal determination of the position of the medical instrument. The position of the medical instrument within the three-dimensional image data record is also calculated by data assignment of the image data generated pre-operatively and intra-operatively. Disadvantages of this method result for example from the cost of additional pre-operative x-ray examinations and the existing installation of a position measuring device.

This results on the one hand in additional examination outlay, in other words in the case of a computed tomography method additional radiation exposure for the patient. Also the position determination can easily be adversely affected if medical personnel cover the reference points for the position determination, which are for example attached in the form of infrared lights. Also the time difference between pre-operative data acquisition and intra-operative data acquisition can result in an inaccurate position determination due to a corresponding change in the state of the patient during this time period.

SUMMARY OF THE INVENTION

The object of the invention is to provide a method of the type described in the introduction, which simplifies graphical representations of medical instruments in objects under examination, particularly with regard to the quantity of electronic data to be processing during this.

In the case of the method of the type described in the introduction the object is achieved by the characterizing features of the claims. The instrument image essentially shows the instrument inserted into the object under examination without background information. Vectorization of the instrument image allows the quantity of data to be reduced, whilst enhancing the quality of representation of the medical instrument and is carried out using an image processing system. The captured linear structure of the instrument image is thereby approximated by polylines.

This is done by determining reference points or interpolation points and a vector assigned respectively to the interpolation point with a length tailored to the line segment. The end of the vector defines a new interpolation point. The characteristics of the polyline, such as color, line thickness, flashing display, etc., can be tailored to the respective conditions of the intervention. On the one hand this method reduces subsequent image processing outlay and therefore computing time. On the other hand medical personnel can work more accurately due to the improved quality. This is of particularly high importance when working with filigree structures in sensitive systems, such as a neurological guide wire in a vascular system in the brain.

In one advantageous embodiment of the invention the instrument image is vectorized electronically. This means that no user interaction is required to capture the medical instrument. The medical instrument is identified automatically from the instrument image and captured by a polyline. This reduces the burden on medical personnel and allows a faster representation due to the reduced quantity of data.

In one preferred development of the invention a time sequence of vectorized instrument images is generated and the difference between two successive polylines respectively is determined. It is thus possible to represent the pattern over time of the site and/or optionally the location of the medical instrument in a graphical manner. The difference between successive vectorized instrument images provides differences between the two polylines in respect of site and location. These allow the change in polyline information over time to be determined. The change in the polyline can be shown in a different manner from the rest of the representation of the polyline, for example by a change in color, flashing, etc. This increases the accuracy of the medical intervention, as the change in the site and location of the medical instrument can be determined at any time. It is also possible to obtain accurate information about sub-segments of the medical instrument or polyline that cross over each other.

In one preferred variant of the invention the change between instrument images is captured by an enlarged image section around the end of the polyline. It is then not necessary to search through the whole image for changes, just a relevant search region, which can be found at the visible ends of the inserted medical instrument. By subtracting these image regions from temporally successive instrument images it is possible to determine the change in the position and location of the polyline. Restricting the search region reduces the outlay required to capture the change and thus the information to be processed to monitor the site and location of the medical instrument in the form of the polyline.

In one advantageous embodiment of the invention the temporal sequence of the images of the medical instrument in the object under examination is backed up electronically. The intervention carried out can thus be monitored subsequently in a virtual manner at a computer, which improves the safety and understanding of the patient with regard to the intervention and can be used for learning processes within the medical team or in medical training.

In a further preferred embodiment of the invention the instrument image is determined by subtracting a reference image showing the object under examination from an overall image showing the medical instrument and the object under examination. The reference image and overall image, which are required to generate the instrument image, can be generated in a different manner.

However the subtraction of images in this manner represents a standard and well-understood method for determining structures and is used successfully in digital subtraction angiography. Given current experience in the field of image subtraction, this method for generating the instrument image is advantageous. The generation of instrument images by means of subtraction methods is one possible method. Further methods for generating an instrument image are filter methods. These can also be used to generate an instrument image.

In a further advantageous variant of the invention the reference image is determined as the image of the object under examination in the absence of the medical instrument. Such a reference image is also known as a mask image. It shows the examination region of interest in the object under examination without the medical instrument. This also reduces the time, for which the medical instrument is inserted into the object under examination.

In a further advantageous embodiment of the invention the overall image is determined without the use of contrast agents. In other words the medical instrument is inserted into the object under examination and an image capturing the medical instrument is acquired. The medical instrument is visible on the acquired image, for example through the use of radio-opaque material. The overall image should show the same content of the object under examination as the mask image, in order to allow simple subtraction. Subtraction of the mask image from the overall image gives the instrument image.

In a further preferred embodiment the reference image is determined as an image capturing the medical instrument without the use of contrast agents. While the reference image is being acquired the medical instrument is already present in the object under examination. Such a procedure is advantageous, if the examination region of interest in the object under examination changes. The reference image background therefore also changes.

With this manner of reference image acquisition it is not essential for the instrument to have at least segments with a radio-opaque characteristic. One advantage compared with the acquisition of a mask image is that should the examination region change beyond specific limits, the instrument inserted into the object under examination does not have to be removed in order to acquire a new mask image of the new or extended examination region. This is not necessary with the method described here, as the reference image is always acquired in the examination region, where the medical instrument is located.

In a further advantageous development the overall image is determined using contrast agents. The introduction of contrast agents into the object under examination or the medical instrument increases the contrast of the environment of the medical instrument or the medical instrument itself. An instrument image can then be generated by means of image subtraction from a reference image capturing the medical instrument and a contrast-enhanced overall image. The sequence of contrast agent introduction can thereby be reversed, in other words the reference image can be acquired with the introduction of contrast agents and the overall image without the introduction of contrast agents. By varying the contrast agent and the sequence of contrast agent introduction it is possible to generate positive or negative images of the medical instrument, which are then vectorized.

In a further advantageous variant of the invention the polyline representing the medical instrument is represented in position and/or optionally location in relation to the position and/or optionally location of the object under examination. The polyline representing the instrument is displayed merged or superimposed on the data of the object under examination. This allows the site and/or orientation of the medical instrument to be determined within the object under examination. The instrument can this always be located in relation to the location of the object under examination. This improves patient safety and makes it easier for medical personnel to plan further progress during the intervention.

In a further preferred embodiment of the invention the polyline is determined with the object under examination as a two-dimensional projection. This allows two-dimensional location with little outlay. The vectorized representation of the medical instrument as a polyline allows it to be clearly differentiated from its environment, in that polyline parameters—such as color, line thickness, etc.—can be tailored and it can therefore be easily identified.

In a further advantageous variant of the invention a spatial representation of the medical instrument with the object under examination is determined from different two-dimensional projections. From the acquisition of the images of the examination region from different directions, for example with a biplanar image, and using algorithms for spatial representation, for example back-projections, it is possible to obtain a spatial representation of the medical instrument or the polyline in the object under examination from two different instrument image projections for the same instrument state.

The examination device for acquiring the images can essentially involve any medical imaging method, in particular x-ray systems, devices which use magnetic fields to generate a graphical representation of an object under examination, as well as ultrasound, etc.

Another option for a spatial representation without intraoperative acquisition of the object under examination is a previously generated 3D vascular model, which was generated as a mean model for a number of patients or ideally represents the vascular model of the patient to be treated. Three-dimensional location of the instrument can also be carried out in the vascular model, using the movement of the medical instrument and the capturing of the associated coordinates and/or coordinate changes. These options for spatial instrument representation in the object under examination assist medical personnel significantly during the medical intervention and primarily reduce the radiation load on the patient in the last-mentioned instance.

In a further preferred development of the invention a spatial representation of the medical instrument with the object under examination is determined for different views. This can be carried out in the context of the possible acquisition angles of the examination device, or by electronic image processing, which generates further views using already determined spatial representations. This can for example be useful when the medical instrument cannot be shown in the required direction by image acquisition, if it or the image acquisition arrangement does not allow this. It also includes enlargements and reductions of images and image sections. Patient radiation exposure can also be reduced in this manner.

BRIEF DESCRIPTION OF THE DRAWINGS

Further advantages of the inventive method in conjunction with an arrangement that is suitable for its implementation will emerge from an exemplary embodiment, which is described in more detail below with reference to the schematic drawings, in which FIG. 2 shows a flow diagram of the inventive method for generating a vectorized instrument image, FIG. 3 shows a flow diagram of the inventive method for determining the change in polyline formation over time.

DETAILED DESCRIPTION OF THE INVENTION

Figure 1:
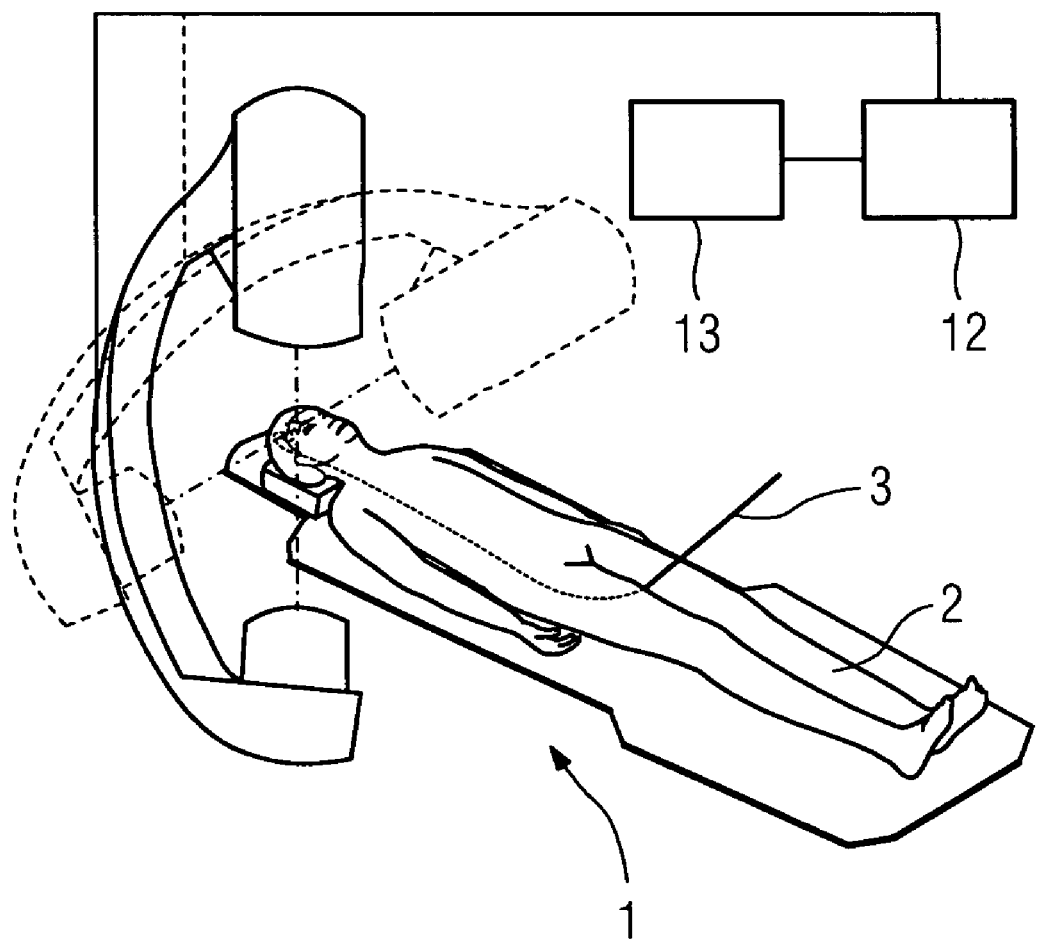
FIG. 1 shows an arrangement for implementing the inventive method.

The arrangement shown in FIG. 1 for implementing the inventive method includes an examination device 1, here comprising a double C-arm x-ray system, having an acquisition device for an object under examination 2. The object under examination 2 is to be disposed on the acquisition device of the examination device 1 for execution of the inventive method such that the isocenter of the examination device 1 comes to lie where possible in the examination region of interest in the object under examination 2.

A medical instrument 3 is inserted into the object under examination 2, configured in the exemplary embodiment as a neurological guide wire. The neurological guide wire 3 is inserted into the vascular system of the object under examination 2 and navigated into the vascular system of the head. To control the intracranial position and location of the guide wire 3 in the object under examination 2, navigation is controlled by the examination device 1.

To this end a reference image 5 is acquired in the absence of the medical instrument 3 from the region of interest in the object under examination 2. As soon as the neurological guide wire 3 is in the environment of the examination region of interest, an overall image 6 (see FIG. 2) of the examination region of interest is acquired with the inserted medical instrument 3. The backgrounds of the reference image 5 (see FIG. 2) and overall image 6 (see FIG. 2) should be acquired with the closest correspondence possible. In proximity to moving objects—e.g. the heart—this can for example be done using a triggering system for the acquisition of images 5 and 6 (see FIG. 2), connected to means (not shown) for capturing data of the object under examination 2 and a controller (also not shown). It is then possible to acquire images 5 and 6 (see FIG. 2) always in the same movement state of the object under examination 2.

For the application of the inventive method to a neurological guide wire 3 the triggering system for the acquisition of images 5 and 6 (see FIG. 2) is of less importance, as rhythmic or arrhythmic movement does not generally occur in the head region of a patient 2. The acquired images 5 and 6 (see FIG. 2) are further processed according to the inventive method and the location and position of the guide wire 3 in the object under examination 2 is determined in an image processing unit 12. The result is displayed on an image output unit 13 and thus made available to the medical personnel.

According to FIG. 2 the reference image 5, a mask image in the exemplary embodiment, and the overall image 6 are represented as the starting point for generation of the instrument image 4. In the exemplary embodiment only the region of interest in the object under examination 2 is visible on the reference image 5, without the medical instrument 3. The overall image 6 shows essentially the same examination region, with the inserted instrument 3 being mapped within the examination region.

The medical instrument 3 is mapped for example in that at least a segment of the guide wire 3 has a radio-opaque characteristic. In the exemplary embodiment the radio-opaque segment is in the end region of the inserted guide wire 3. The end of the medical instrument 3 can also be provided with a marking (not shown in the exemplary embodiment) that can be identified on the overall image 6, so that the end of the medical instrument 3 can always be clearly identified. The images 5 and 6 are fed to the image processing unit 12 (see FIG. 1), in which subtraction S is carried out and the data is backed up.

The method step of subtraction S allows the background of the images 5 and 6, in other words the information about the object under examination 2, to be removed. The resulting image is the instrument image 4. The linear structure of the guide wire 3 is mapped on this. Vectorization V of the medical instrument 3 shown in the instrument image 4 produces a vectorized instrument image 7, in which the visible medical instrument 3 is approximated automatically as a polyline and displayed.

Because the examination device 1 is in the form of a double C-arm x-ray system, two reference images 4 or two overall images 5 of the object under examination 2 or the object under examination 2 with the inserted medical instrument 3 can be acquired simultaneously. Generation of the vectorized instrument image 7 from a second projection direction, which is different from the first, is a requirement for the spatial representation of the polyline 8 in the object under examination 2. Back-projection can be used to generate a spatial representation of the polyline 8. The polyline 8 is superimposed with the spatial representation of the examination region also generated in the image processing unit 12 and identified using color, for example to be more clearly recognizable in the merged image, to stand out from the object under examination 2. This representation is transmitted to the image output unit 13 and thus made available to medical personnel.

The presence of a reference image 5 and an overall image 6 is necessary when an instrument image 4 is generated by subtraction S of these images 5 and 6 from each other, as in the exemplary embodiment. However the reference image 5, overall image 6 and method step of subtraction S only form one optional element of the inventive method. In contrast the generation of an instrument image 4, which is defined in that it can be used to generate a polyline 8 representing the instrument 3, is required.

FIG. 3 shows two vectorized instrument images 7 and 7' as the starting point for determining the change in polyline formation over time, these being more specifically a temporally previous instrument image 7 and a temporally subsequent instrument image 7'. The temporally previous vectorized instrument image 7 shows a polyline 8, having an end 9. The temporally subsequent vectorized instrument image 7' shows the same polyline 8', but in a modified formation, as the end 9' of the polyline 8' has moved further.

The environment of the ends 9 and 9' of the polyline 8 and 8' of the temporally previous or subsequent vectorized instrument image 7 and 7' can optionally be enlarged to reduce the quantity of data for image subtraction S. This is done by a section enlargement A. The temporally previous section image 7A results. The same image section is enlarged in the temporally subsequent instrument image 7'. The temporally subsequent section image 7A' results. The method step of image subtraction S of the images 7A and 7A' provides the change 11 in polyline formation in the time between the temporally previous and subsequent vectorized instrument images 7 and 7', which is shown in a differential image 10.

This image can be superimposed with the already generated images 4, to display the change in the polyline 8 and 8' on the image output unit 13. The change in the polyline formation can for example be highlighted separately in the spatial representation, perhaps by a flashing display of the changes in the polyline formation in the object under examination 2.

Provision is also made for the image processing unit 12 to allow a free selection of views of the guide wire 3 with the object under examination 2. This involves free rotation of the representation in all spatial directions, zooms, cross-sectional views, etc. This allows medical personnel to make the best possible assessment of the current situation in the object under examination 2.

The invention claimed is:

1. A method for graphically determining change in position of a medical instrument during a medical procedure, comprising:
   inserting the medical instrument at least partially into an object under the examination;
   generating and displaying a temporal sequence of images of the medical instrument for virtual monitoring of instrument positioning during the procedure, wherein each instrument image is vectorized prior to display by transforming each image of the medical instrument into a polyline image formation; and
   performing, during the procedure, an image subtraction between two of the polyline image formations to generate and display a differential image indicating temporal change in the instrument position.

2. The method as claimed in claim 1, wherein the vectorization of each instrument image is performed electronically and the image subtraction is performed by subtracting data corresponding to an end portion of a first polyline image formation from data corresponding to an end portion of a second polyline image formation.

3. The method as claimed in claim 2, wherein each in the temporal sequence of vectorized instrument images is generated independent of the other and the image subtraction is based on a change between two successive, independently defined polylines.

4. The method as claimed in claim 3, wherein the change is determined by comparing only enlarged image sections of the two end portions of the first and second polylines.

5. The method as claimed in claim 1, wherein the step of generating and displaying a temporal sequence of images includes, for each generated instrument image subtracting a reference image of the object from an overall image of the object.

6. The method as claimed in claim 5, wherein the reference image is an image of the object without the medical instrument inserted into the object and the overall image is an image of the object with the medical instrument inserted into the object.

7. The method as claimed in claim 6, wherein the overall image is generated without a contrast agent.

8. The method as claimed in claim 7, wherein the medical instrument is visible on the overall image by using a radio-opaque material or a marker.

9. The method as claimed in claim 5,
   wherein the reference image is an image of the object without the medical instrument inserted into the object and is generated without a contrast agent, and
   wherein the overall image is an image of the object with the medical instrument inserted into the object and is generated with a contrast agent.

10. The method as claimed in claim 5,
    wherein the reference image is an image of the object with the medical instrument inserted into the object and is generated with a contrast agent, and
    wherein the overall image is an image of the object with the medical instrument inserted into the object and is generated without a contrast agent.

11. The method as claimed in claim 1, wherein the polylines are two-dimensional projections.

12. The method as claimed in claim 11, wherein a spatial representation of the medical instrument is determined from different two-dimensional projections.

13. The method as claimed in claim 12, wherein the spatial representation of the medical instrument is determined for different views.

14. The method as claimed in claim 1, wherein the polylines are three-dimensional projections determined by a three-dimensional image model of the object generated prior to performing the examination procedure.

* * * * *